(12) United States Patent
Konno

(10) Patent No.: US 11,039,922 B2
(45) Date of Patent: Jun. 22, 2021

(54) PROSTHETIC HEART VALVE FOR TRANSCATHETER HEART VALVE IMPLANTATION

(71) Applicant: Edwards Lifesciences Corporation, Irvine, CA (US)

(72) Inventor: Mark A. Konno, Laguna Beach, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 44 days.

(21) Appl. No.: 16/356,509

(22) Filed: Mar. 18, 2019

(65) Prior Publication Data

US 2019/0209319 A1    Jul. 11, 2019

Related U.S. Application Data

(63) Continuation of application No. 15/132,137, filed on Apr. 18, 2016, now Pat. No. 10,231,836, which is a
(Continued)

(51) Int. Cl.
*A61F 2/24* (2006.01)
*A61F 2/958* (2013.01)

(52) U.S. Cl.
CPC .......... *A61F 2/2442* (2013.01); *A61F 2/2409* (2013.01); *A61F 2/2412* (2013.01); *A61F 2/2418* (2013.01); *A61F 2/2433* (2013.01); *A61F 2/2445* (2013.01); *A61F 2/2427* (2013.01); *A61F 2/958* (2013.01); *A61F 2220/0075* (2013.01); *A61F 2230/0034* (2013.01); *A61F 2250/001* (2013.01); *A61F 2250/0071* (2013.01)

(58) Field of Classification Search
CPC ................................ A61F 2/24; A61F 2/2442
See application file for complete search history.

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| EP | 0338994 A1 | 10/1989 |
| EP | 1034753 A1 | 9/2000 |

(Continued)

OTHER PUBLICATIONS

Extended European Search Report from corresponding international application No. PCT/US2009/057715 dated Nov. 14, 2012.
(Continued)

*Primary Examiner* — Matthew W Schall
(74) *Attorney, Agent, or Firm* — Guy Cumberbatch

(57) ABSTRACT

A prosthetic heart valve, and associated methods therefore, configured to replace a native heart valve, and having a support frame configured to be reshaped into an expanded form in order to receive and/or support an expandable prosthetic heart valve therein. The prosthetic heart valve may be configured to have a generally rigid and/or expansion-resistant configuration when initially implanted to replace a native valve (or other prosthetic heart valve), but to assume a generally non-rigid and/or expanded/expandable form when subjected to an outward force such as that provided by a dilation balloon.

20 Claims, 9 Drawing Sheets

Related U.S. Application Data continuation of application No. 12/234,559, filed on Sep. 19, 2008, now Pat. No. 9,314,335.

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,348,068 B1 | 2/2002 | Campbell et al. |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,524,330 B2 | 4/2009 | Berreklouw |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,780,723 B2 | 8/2010 | Taylor |
| 7,806,927 B2 | 10/2010 | Styrc |
| 7,871,436 B2 | 1/2011 | Ryan et al. |
| 8,226,707 B2 | 7/2012 | White |
| 8,246,677 B2 | 8/2012 | Ryan |
| 8,496,700 B2 | 7/2013 | Edoga et al. |
| 8,500,802 B2 | 8/2013 | Lane et al. |
| 2001/0021874 A1 | 9/2001 | Carpentier et al. |
| 2002/0062150 A1 | 5/2002 | Campbell et al. |
| 2003/0033009 A1 | 2/2003 | Gabbay |
| 2003/0040793 A1 | 2/2003 | Marquez |
| 2003/0199971 A1 | 10/2003 | Tower et al. |
| 2004/0210305 A1 | 10/2004 | Shu et al. |
| 2004/0249452 A1 | 12/2004 | Adams et al. |
| 2004/0249453 A1 | 12/2004 | Cartledge et al. |
| 2005/0096739 A1 | 5/2005 | Cao |
| 2005/0131533 A1 | 6/2005 | Alfieri et al. |
| 2005/0240200 A1 | 10/2005 | Bergheim |
| 2005/0251251 A1 | 11/2005 | Cribier |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2006/0052867 A1 | 3/2006 | Revuelta et al. |
| 2007/0016287 A1 | 1/2007 | Cartledge et al. |
| 2007/0067029 A1 | 3/2007 | Gabbay |
| 2007/0100441 A1 | 5/2007 | Kron et al. |
| 2007/0142907 A1 | 6/2007 | Moaddeb et al. |
| 2007/0162111 A1 | 7/2007 | Fukamachi et al. |
| 2007/0244546 A1 | 10/2007 | Francis |
| 2008/0027483 A1 | 1/2008 | Cartledge et al. |
| 2008/0114452 A1 | 5/2008 | Gabbay |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Iobbi |
| 2008/0275549 A1 | 11/2008 | Rowe |
| 2009/0005663 A1 | 1/2009 | Goetz et al. |
| 2009/0082857 A1 | 3/2009 | Lashinski et al. |
| 2009/0093676 A1 | 4/2009 | Nitzan et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192606 A1 | 7/2009 | Gloss et al. |
| 2009/0216322 A1 | 8/2009 | Le et al. |
| 2009/0281609 A1 | 11/2009 | Benichou et al. |
| 2010/0076548 A1 | 3/2010 | Konno |
| 2010/0076549 A1 | 3/2010 | Keidar et al. |
| 2011/0166636 A1 | 7/2011 | Rowe |
| 2011/0178597 A9 | 7/2011 | Navia et al. |
| 2011/0264207 A1 | 10/2011 | Bonhoeffer et al. |

FOREIGN PATENT DOCUMENTS

| | | |
|---|---|---|
| EP | 1755459 A2 | 2/2007 |
| EP | 1804726 A1 | 7/2007 |
| EP | 1958598 A1 | 8/2008 |

OTHER PUBLICATIONS

PCT International Search Report for PCT App. No. PCT/US2009/057724 (PCT equivalent of U.S. Appl. No. 12/234,580); dated Apr. 13, 2010.

(56) References Cited

OTHER PUBLICATIONS

PCT Written Opinion of the International Searching Authority for PCT App. No. PCT/ US2009/57724 (PCT equivalent of U.S. Appl. No. 12/234,580); dated Apr. 13, 2010.

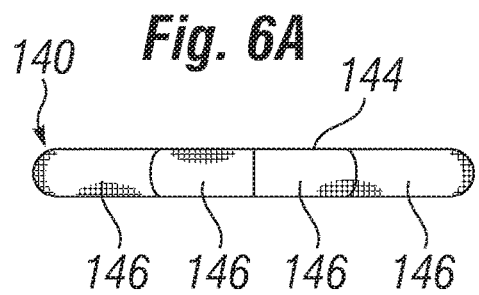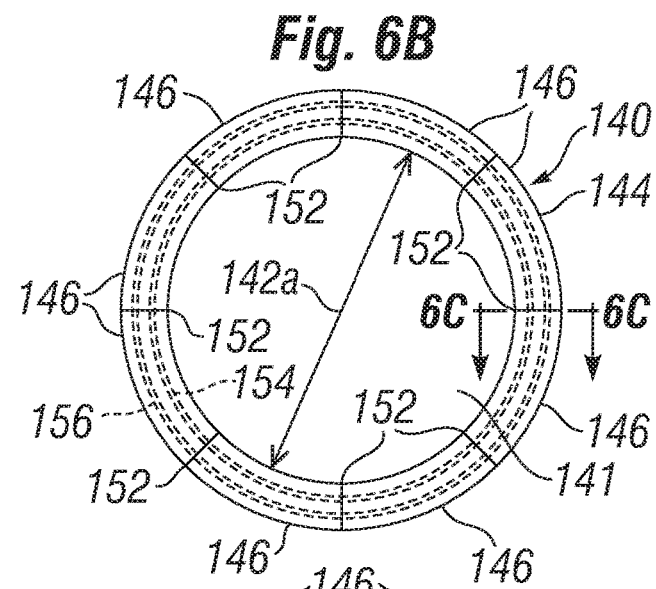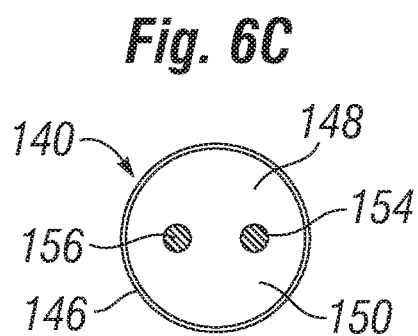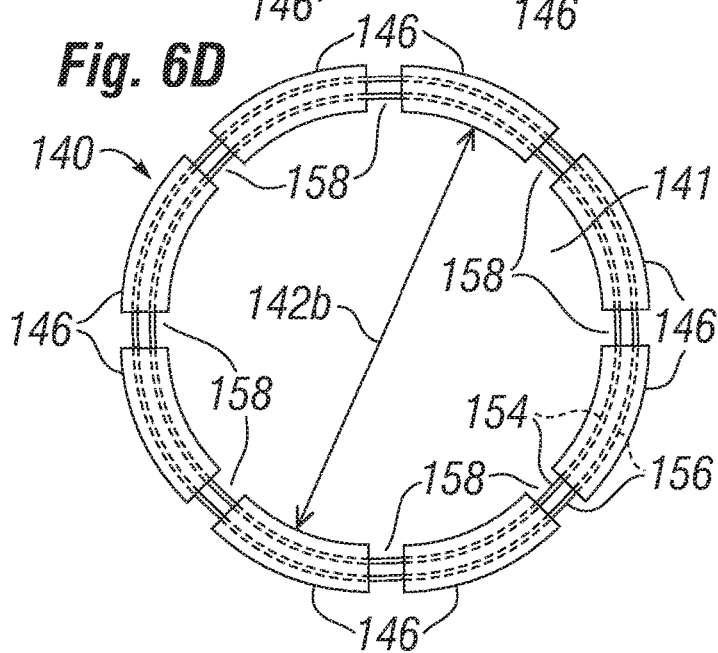

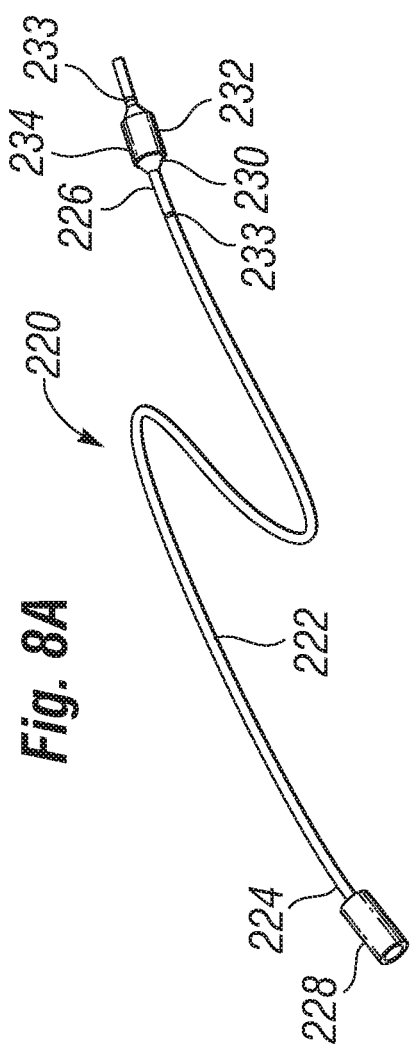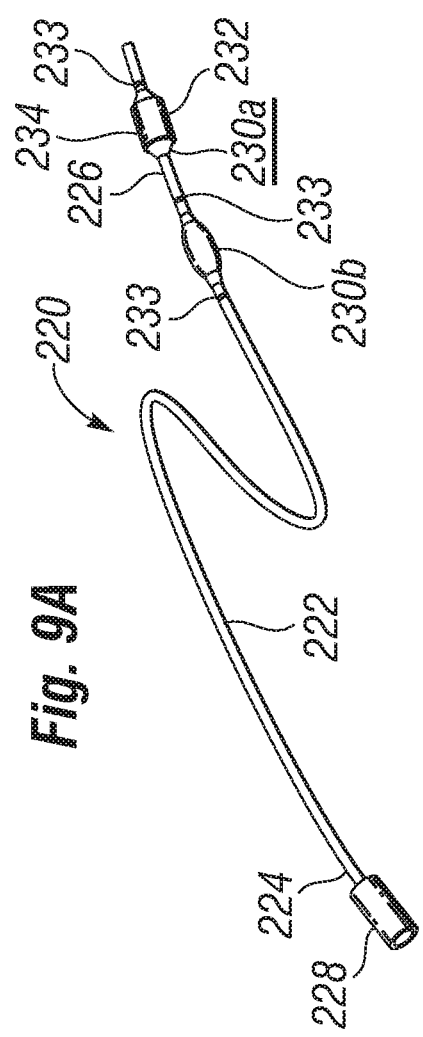

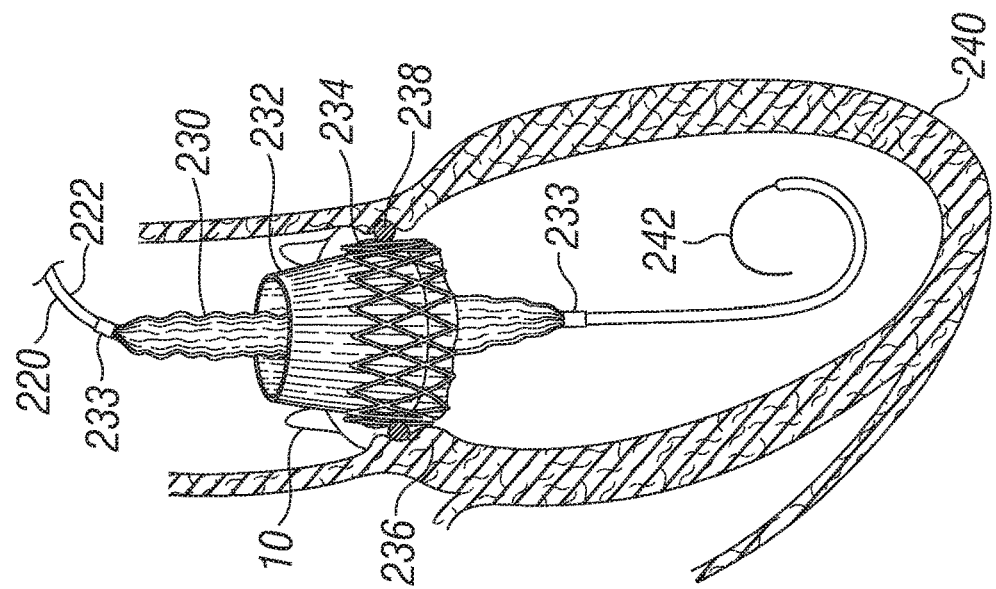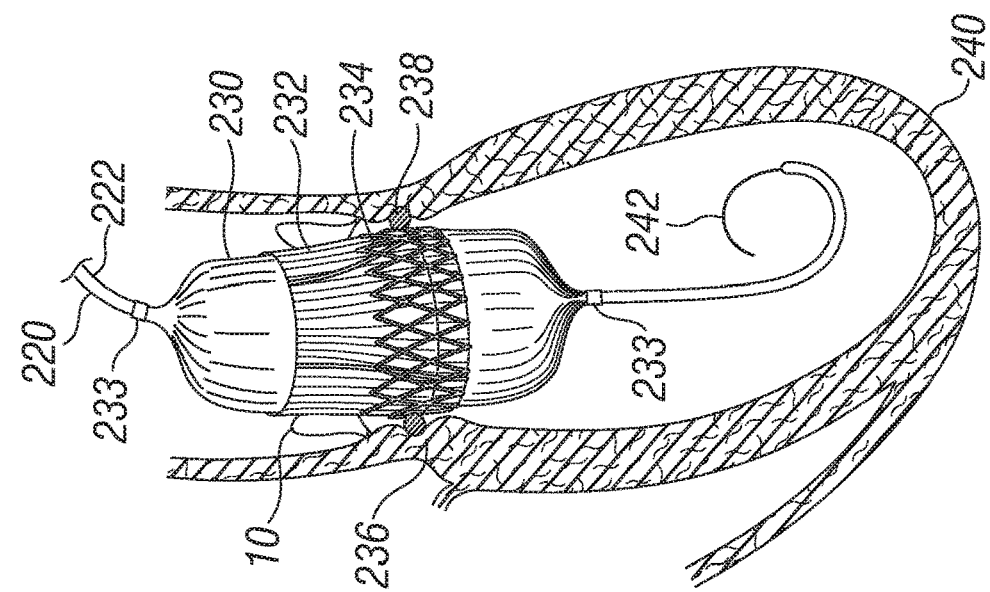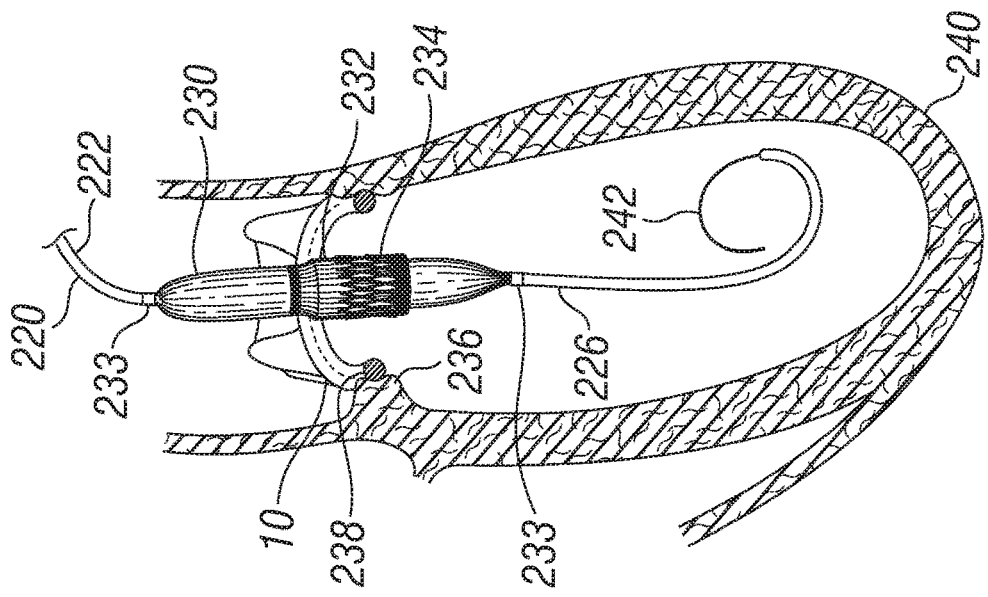

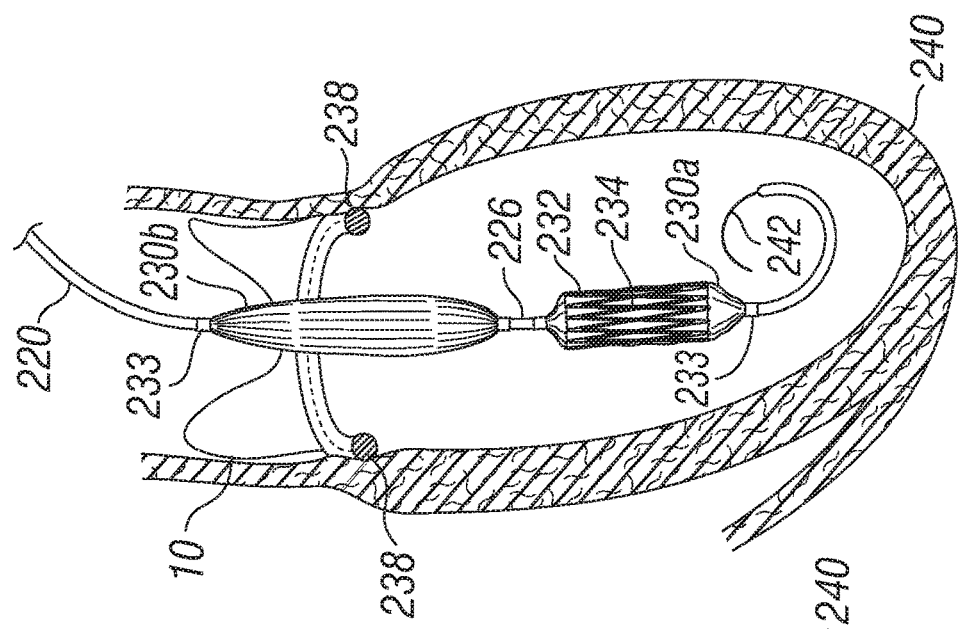
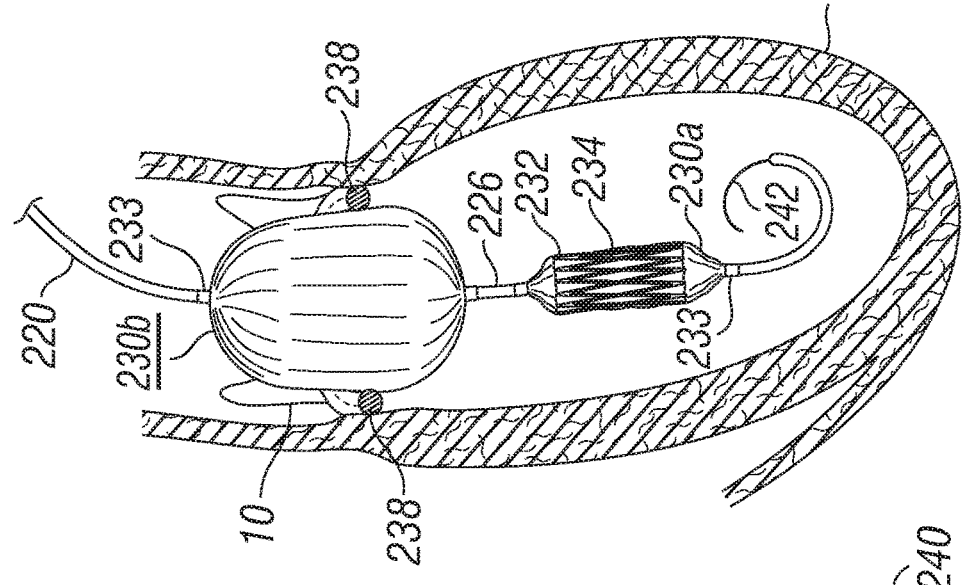
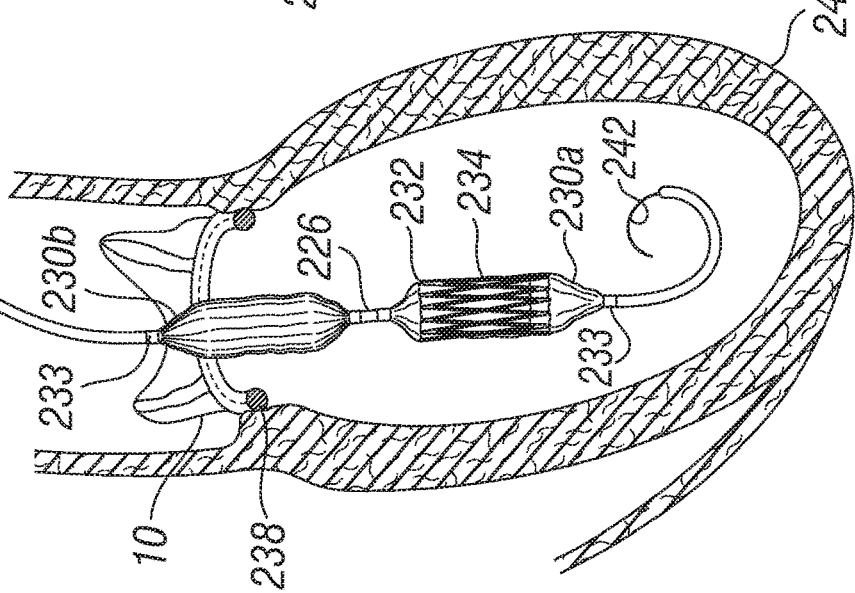

PROSTHETIC HEART VALVE FOR TRANSCATHETER HEART VALVE IMPLANTATION

CROSS REFERENCE TO RELATED APPLICATIONS

This application is a continuation of U.S. patent application Ser. No. 15/132,137, filed Apr. 18, 2016, now U.S. Pat. No. 10,231,836, which is a continuation of U.S. patent application Ser. No. 12/234,559, filed Sep. 19, 2008, now U.S. Pat. No. 9,314,335, the entire contents of each of which are incorporated herein by reference.

FIELD OF THE INVENTION

The present invention relates to a prosthetic heart valve for heart valve replacement, and more particularly to a prosthetic heart valve configured to receive an expandable prosthetic heart valve therein.

BACKGROUND OF THE INVENTION

In humans and other vertebrate animals, the heart is a hollow muscular organ having four pumping chambers separated by four heart valves: aortic, mitral (or bicuspid), tricuspid, and pulmonary. The valves open and close in response to a pressure gradient during each cardiac cycle of relaxation and contraction to control the flow of blood to a particular region of the heart and/or to blood vessels (pulmonary, aorta, etc.)

These valves are comprised of a dense fibrous ring known as the annulus, and leaflets or cusps attached to the annulus. For some valves, there is also a complex of chordae tendineae and papillary muscles securing the leaflets. The size of the leaflets or cusps is such that when the heart contracts the resulting increased blood pressure formed within heart chamber forces the leaflets open to allow flow from the heart chamber. As the pressure in the heart chamber subsides, the pressure in the subsequent chamber or blood vessel becomes dominant, and presses back against the leaflets. As a result, the leaflets or cusps come in apposition to each other, thereby closing the passage.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to replace or repair a diseased or damaged valve. In a traditional valve replacement operation, the damaged leaflets are typically excised and the annulus sculpted to receive a replacement prosthetic valve.

In many patients who suffer from dysfunction of the mitral and/or tricuspid valves(s) of the heart, surgical repair of the valve (i.e., "valvuloplasty") is a desirable alternative to valve replacement. For some patients, however, the condition of the native heart valve requires complete replacement using a prosthetic heart valve. Prosthetic heart valves have been known for some time, and have been successfully implanted using traditional open-chest surgical approaches, minimally-invasive procedures, and so-called percutaneous methods.

A prosthetic heart valve typically comprises a support structure (such as a ring and/or stent) with a valve assembly deployed therein. The support structure is often rigid, and can be formed of various biocompatible materials, including metals, plastics, ceramics, etc. Two primary types of "conventional" heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the entire disclosures of which are hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. Components of the valve are usually assembled with one or more biocompatible fabric (e.g., Dacron) coverings, and a fabric-covered sewing ring is provided on the inflow end of the peripheral support structure.

In many bioprosthetic-type valves, a metallic or polymeric structure provides base support for the flexible leaflets, which extend therefrom. One such support is a "support frame," sometimes called a "wireform" or "stent," which has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus. One example of the construction of a flexible leaflet valve is seen in U.S. Pat. No. 6,585,766 to Huynh, et al. (issued Jul. 1, 2003), in which the exploded view of FIG. 1 illustrates a fabric-covered wireform 54 and a fabric-covered support stent 56 on either side of a leaflet subassembly 52. The contents of U.S. Pat. No. 6,585,766 are hereby incorporated by reference in their entirety. Other examples of valve and related assemblies/systems are found in U.S. Pat. No. 7,137,184, which issued on Nov. 21, 2006, the contents of which are hereby incorporated by reference in their entirety.

Sometimes the need for complete valve replacement may arise after a patient has already had an earlier valve replacement for the same valve. For example, a prosthetic heart that was successfully implanted to replace a native valve may itself suffer damage and/or wear and tear many years after initially being implanted.

Implanting a prosthetic heart valve into a patient with a previously-implanted prosthetic heart valve typically involves additional steps from a similar procedure in a patient with no previously-implanted heart valve. Implanting the prosthetic heart valve directly within a previously-implanted prosthetic heart valve is generally impractical, in part because the new prosthetic heart valve (including the support structure and valve assembly) will have to reside within the annulus of the previously-implanted heart valve, and traditional prosthetic heart valves are not configured to easily receive such a valve-within-a-valve implantation in a manner which provides secure seating for the new valve while also having a large enough annulus within the new valve to support proper blood flow therethrough. Implanting a prosthetic heart valve in a patient who previously had a prosthetic heart valve generally requires the previously-implanted heart valve to be removed during the same procedure in which the new prosthetic heart valve is implanted. In such cases, a surgeon can use a traditional surgical approach to install the prosthetic valve, which can involve the surgeon cutting out the previously-implanted heart valve from the heart valve annulus, and then implanting the new prosthetic valve into the heart valve annulus.

Percutaneous and minimally-invasive heart valve replacement has been developed recently, wherein a prosthetic heart valve is advanced percutaneously (e.g., via the femoral artery or other desired approaches) or via other approaches (i e, minimally-invasive "keyhole" surgery, including approaches via the apex of the heart, etc.) into the heart valve annulus, and then expanded within the heart valve annulus. Various expandable valves are being tested, primarily that use balloon- or self-expanding stents as anchors. For the purpose of inclusivity, the entire field will be denoted herein as the delivery and implantation of expandable valves, regardless of whether the delivery method involves percutaneous, minimally-invasive, or other delivery methods. These valves typically include a scaffold or frame that expands radially outward into direct anchoring contact with the annulus, sometimes assisted with barbs. Examples of percutaneous heart valves and delivery systems and methods therefore are described in U.S. Pat. No. 5,411,552, issued May 2, 1995; U.S. Pat. No. 5,840,081, issued Nov. 24, 1998; U.S. Pat. No. 6,168,614, issued Jan. 2, 2001; and U.S. Pat. No. 6,582,462, issued Jun. 24, 2003; and also in U.S. patent application Ser. No. 11/280,062, filed Nov. 16, 2005; U.S. patent application Ser. No. 11/488,510, filed Jul. 18, 2006; and U.S. patent application Ser. No. 11/542,087, filed Oct. 2, 2006; the contents of each of which are hereby incorporated by reference in their entirety.

Percutaneous heart valve replacement is often performed without cutting out the native heart valve, wherein the prosthetic heart valve is expanded in the native heart valve annulus and the native valve leaflets are pressed against the valve annulus walls by the expanded prosthetic heart valve. However, in cases where a previously-implanted prosthetic heart valve is present, deploying a prosthetic heart valve within the native heart valve may be impractical. The shape and structure of the previously-installed prosthetic heart valve may interfere with the proper placement, deployment, and functioning of the new prosthetic heart valve.

There is thus a need for a prosthetic heart valve which will properly replace a damaged heart valve, but will also enable a replacement expandable prosthetic heart valve to be deployed therein at a later time. The current invention meets this need.

SUMMARY OF THE INVENTION

The invention is a prosthetic heart valve configured to receive a prosthetic heart valve, such as a catheter-deployed (transcatheter) prosthetic heart valve, therein. In one embodiment, the prosthetic heart valve has a support structure which is generally resistant to expansion when deployed in the patient's native heart valve annulus to replace the native heart valve (or to replace another prosthetic heart valve), but is configured to transform to a generally expanded and/or expandable configuration in order to receive a prosthetic heart valve therein. The transformation from expansion-resistant to expanded/expandable can be achieved by subjecting the expansion-resistant support structure to an outward force, such as a dilation force, which may be provided by a dilation balloon used to deploy a replacement prosthetic valve.

The prosthetic heart valve structure may be generally rigid prior to dilation, and may be configured to become generally non-rigid, and even generally elastic, when subjected to an outward force. The elasticity may assist in holding a percutaneously-introduced prosthetic valve within the current prosthetic valve structure.

The prosthetic valve can be initially deployed in the patient's valve annulus using various surgical techniques (e.g., traditional open-chest, minimally-invasive, percutaneous, etc.) to correct heart valve function. If the heart valve function declines further after deployment of the prosthetic valve, a new replacement prosthetic valve can be deployed within the previously-deployed prosthetic valve without the need to excise the previously-deployed prosthetic valve. Deployment of the replacement prosthetic valve within the previously-deployed prosthetic valve can occur at a much later time from initial deployment of the previously-deployed prosthetic valve. The prosthetic valve of the current invention is configured to be deployed in a patient and, at a later time, to accept and even improve deployment of a replacement prosthetic valve within the same valve annulus.

In one embodiment, the structure can include a core comprising a spring, a plastically deformable material (including breakable materials), etc. The core may be formed as a single piece (possibly with one or more weakened sections configured to fail when subjected to a sufficient force), or may be formed from several segments connected at seams. The core may form an inner lumen through which further attachment devices may be passed, such as elastic and/or inelastic cords.

A prosthetic valve according to an embodiment of the invention may include a cover configured to hold the core together after it has been dilated. For example, where a core breaks into multiple pieces during dilation, the cover can serve to keep the pieces from separating from the prosthetic valve. The cover can also serve to hold the core and/or other portions of the support frame in a desired shape, and may have elastic properties.

In an embodiment of the invention, the prosthetic valve is a stented bioprosthetic valve configured to expand and contract dynamically within the patient's annulus. The dynamic motion of the annulus can enable the valve opening to expand during periods of peak demand, and reduce the annular restriction to the increased flow. The expansion can also decrease leaflet stresses associated with potential higher gradients. The expansion can also permit later placement of an expandable prosthetic valve within the stented bioprosthetic valve.

In an embodiment of the invention, a prosthetic valve has a support structure having a generally rigid and/or expansion-resistant portion including a core. The prosthetic valve may include plastically deformable materials configured to maintain the prosthetic valve support structure in the generally rigid and/or expansion-resistant shape for deployment. The plastically deformable materials may be configured to break or otherwise plastically deform and no longer maintain the support structure in the generally rigid and/or expansion-resistant configuration when subjected to a dilation force. The support structure may form a continuous loop, and may include elastically deformable material configured to provide tension about the continuous loop after the support structure has been dilated by a dilation balloon.

A method for repairing a patient's heart function according to an embodiment of the invention can include: providing a prosthetic heart valve configured to have a generally rigid and/or expansion-resistant support structure upon implantation and also configured to assume a generally non-rigid and/or expanded/expandable configuration upon dilation; and implanting the prosthetic heart valve in a heart valve annulus. The method may also include deploying an expandable prosthetic heart valve within the previously-deployed heart valve and heart valve annulus. Deploying the expandable prosthetic heart valve within the previously-deployed prosthetic valve and heart valve annulus may include dilating the previously-deployed prosthetic valve to cause the previously-deployed prosthetic valve to assume a generally non-rigid and/or expanded/expandable shape.

Dilating a previously-deployed prosthetic heart valve may include using a dilation balloon, such as the type currently used for dilation of native heart valves, which can be advanced within the previously-deployed prosthetic heart valve and expanded to a desired pressure and/or diameter. As a general rule, dilation balloons used for dilation of native valves are formed from generally inelastic material to provide a generally fixed (i.e., pre-set) outer diameter when inflated. Once such balloons are inflated to their full fixed diameter, they will not appreciably expand further (prior to rupturing) even if additional volume/pressure is added therein. Typical pressures for inflating such balloons are between 1 and 6 atmospheres, with pre-set inflated outer diameters of such balloons being on the order of 18 to 33 millimeters. The dilation balloon may be expanded to a desired pressure (e.g., 1-6 atmospheres) sufficient to fully inflate the dilation balloon to its desired diameter and to dilate and expand the previously-deployed prosthetic heart valve.

A typical surgically-implanted prosthetic heart valve will withstand dilation pressures of several atmospheres such as provided by most dilation balloons without expanding and/or becoming elastic. By contrast, the prosthetic heart valve of the current invention is configured to become expanded and/or generally elastic when subjected to sufficient pressure provided by a dilation balloon. If the dilation balloon is expanded, using sufficient pressure, to an expanded outer diameter larger than the inner diameter of the prosthetic heart valve of the invention, the prosthetic heart valve will expand in diameter and/or become elastic.

In one embodiment, the dilation balloon is configured with a pre-set inflated outer diameter which is larger, such as by 10-20% or more, than the inner diameter of the previously-deployed prosthetic heart valve. As an example, if the previously-deployed prosthetic heart valve of the invention has an inner diameter of 23 mm, a dilation balloon having an inflated diameter of 24-27 mm may be inflated within the prosthetic heart valve to cause it to expand and/or become elastic.

Prosthetic heart valves according to various embodiments of the invention can be configured to be generally rigid prior to dilation, but become expanded and/or elastic when subjected to a sufficient dilation pressure. For example, a prosthetic heart valve could be configured to withstand naturally occurring dilation pressures that may occur during beating of the heart, but to become expanded and/or elastic when subjected to a desired pressure (e.g., from a dilation balloon), such as a pressure of 1 atmosphere, 2 atmospheres, 3 atmospheres, 4 atmospheres, 5 atmospheres, or 6 atmospheres, depending on the particular application.

Note that the dilation balloon inflated diameters and inflated pressures, as well as the pressures at which the prosthetic heart valve of the invention would become expanded and/or elastic, set forth above are by way of example, and that the use of balloons with other pressures and diameters, and of prosthetic heart valves configured to change shape and/or expand and/or become elastic when subjected to other pressures and expanded balloon diameters, are also within the scope of the invention.

An annuloplasty ring is being developed having a structure that can expand and/or otherwise change configuration in order to accept a percutaneously-delivered prosthetic heart valve therein. Such an annuloplasty ring is disclosed in U.S. patent application Ser. No. 12/234,580 filed concurrently herewith and entitled "Annuloplasty Ring Configured to Receive a Percutaneous Prosthetic Heart Valve Implantation," the entire contents of which are incorporated herein by reference.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 6A-6C depict top, side, and close-up sectional views, respectively, of a prosthetic heart valve support structure according to an embodiment of the invention;

FIG. 6D depicts a top view of the prosthetic heart valve support structure of FIGS. 6A-6C after the prosthetic heart valve support structure has been dilated;

FIG. 8A depicts an expandable prosthetic heart valve deployment catheter configured for annuloplasty ring dilation and expandable prosthetic heart valve deployment according to an embodiment of the invention;

FIG. 8B depicts the expandable prosthetic heart valve deployment catheter of FIG. 8A positioned within a previously-deployed prosthetic heart valve in a heart valve annulus of a patient according to an embodiment of the invention;

FIG. 8C depicts the expandable prosthetic heart valve deployment catheter of FIG. 8A dilating the previously-deployed prosthetic heart valve and deploying an expandable prosthetic heart valve therewithin according to an embodiment of the invention;

FIG. 8D depicts the expandable prosthetic heart valve deployment catheter of FIG. 8A being withdrawn from the patient according to an embodiment of the invention;

FIG. 9A depicts an expandable prosthetic heart valve deployment catheter configured for dilation of a previously-deployed prosthetic heart valve and for deployment of an expandable prosthetic heart valve according to an embodiment of the invention;

FIG. 9B depicts the expandable prosthetic heart valve deployment catheter of FIG. 9A with the dilation balloon positioned within the previously-deployed prosthetic heart valve in the heart valve annulus according to an embodiment of the invention;

FIG. 9C depicts the expandable prosthetic heart valve deployment catheter of FIG. 9A dilating the previously-deployed prosthetic heart valve according to an embodiment of the invention; and FIG. 9D depicts the expandable prosthetic heart valve deployment catheter of FIG. 9A with the dilation balloon deflated after dilation of the previously-deployed prosthetic heart valve according to an embodiment of the invention.

DETAILED DESCRIPTION OF PREFERRED EMBODIMENTS

Figure 1:
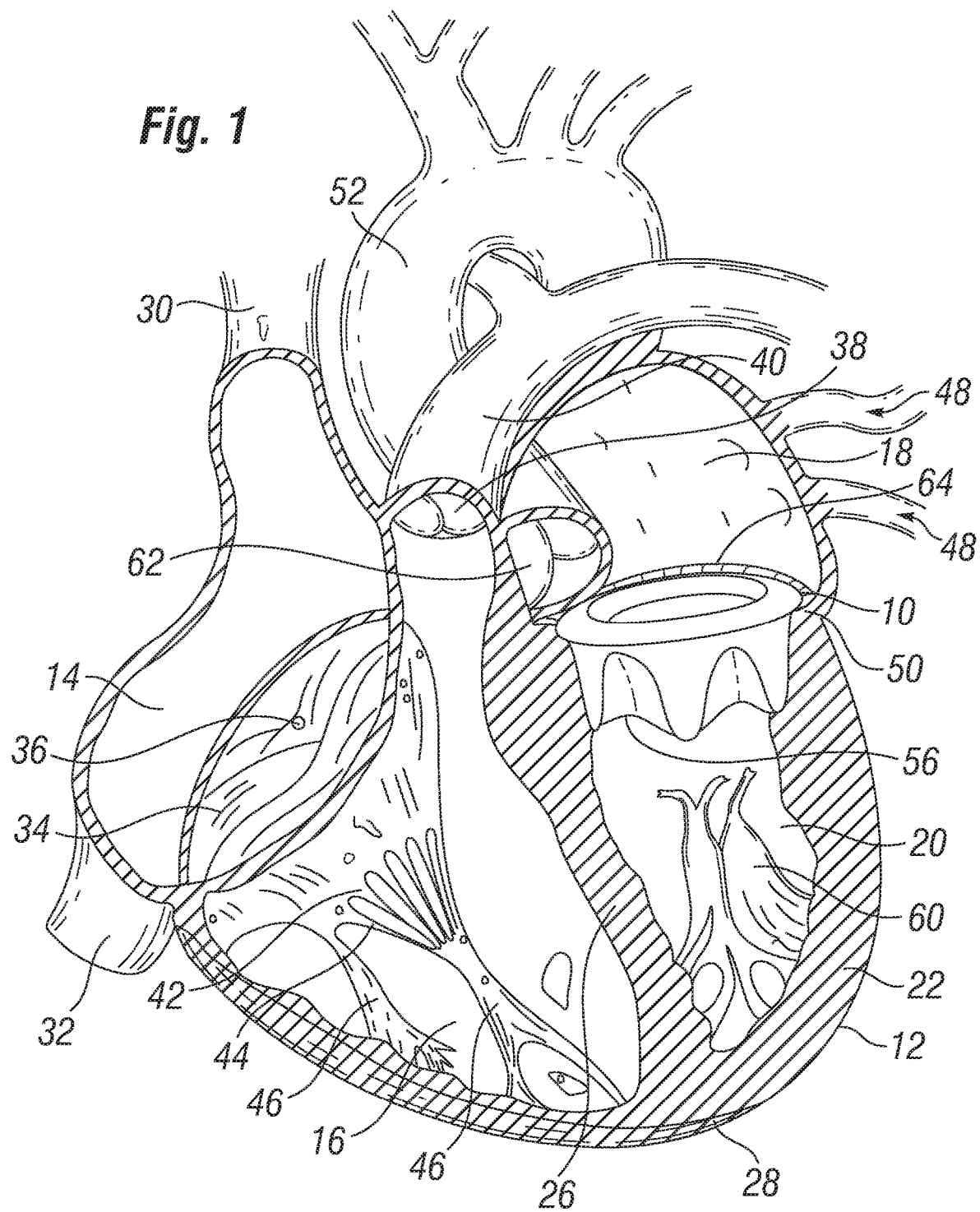
FIG. 1 depicts a prosthetic heart valve deployed in a heart according to an embodiment of the invention.

With reference to FIG. 1, a prosthetic heart valve 10 according to the invention is depicted in a heart 12. The heart 12 has four chambers, known as the right atrium 14, right ventricle 16, left atrium 18, and left ventricle 20. The general anatomy of the heart 12, which is depicted as viewed from the front of a patient, will be described for background purposes. The heart 12 has a muscular outer wall 22, with an interatrial septum 24 dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendineae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve in a normal heart controls blood flow between the left atrium 18 and the left ventricle 20. Note that in the current figure, the native mitral valve has been replaced with the prosthetic heart valve 10, which is accordingly a prosthetic mitral valve 50. The prosthetic mitral valve 50 is closed during ventricular systole when blood is ejected from the left ventricle 20 into the aorta 52. Thereafter, the prosthetic mitral valve 50 is opened to refill the left ventricle 20 with blood from the left atrium 18. Blood from the left ventricle 20 is pumped by power created from the musculature of the heart wall 22 and the muscular interventricular septum 26 through the aortic valve 62 into the aorta 52 which branches into arteries leading to all parts of the body.

In the particular embodiment depicted, the prosthetic heart valve 10 is deployed to replace a native mitral valve, and more particularly is secured (via, e.g., sutures) adjacent and around the mitral valve annulus 64. Depending on the particular application, including the method by which the prosthetic heart valve 10 was implanted, the particular native valve (mitral, tricuspid, etc.) and/or some or all of its associated structures may be entirely or partially removed prior to or during implantation of the prosthetic heart valve 10, or the native valve and/or some or all associated structures may simply be left in place with the prosthetic heart valve 10 installed over the native valve. For example, a native mitral valve typically has two leaflets (anterior leaflet and posterior leaflet), lower portions and free edges of which are connected via mitral chordae tendineae to papillary muscles 60 in the left ventricle 20 for controlling the movements of the mitral valve. Not all of these structures (i.e., mitral valve leaflets, chordae tendineae) are depicted in FIG. 1 because, in the particular embodiment, the native mitral valve and many associated structures (chordae, etc.) have been removed prior to or during implantation of the prosthetic heart valve 10. However, in many prosthetic valve implantations, surgeons choose to preserve many of the chordae tendineae, etc., even when excising the native valve.

Although FIG. 1 depicts a prosthetic mitral valve, note that the invention can be applied to prosthetic valves (and systems and methods therefore) configured to replacement of any heart valves, including aortic, mitral, tricuspid, and pulmonary valves.

Figure 2A:
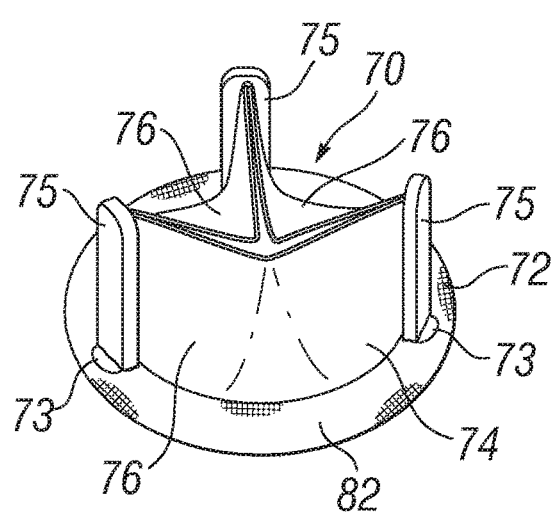
FIGS. 2A-2C depict perspective, top, and side views, respectively, of a prosthetic heart valve according to an embodiment of the invention.
Figure 2B:
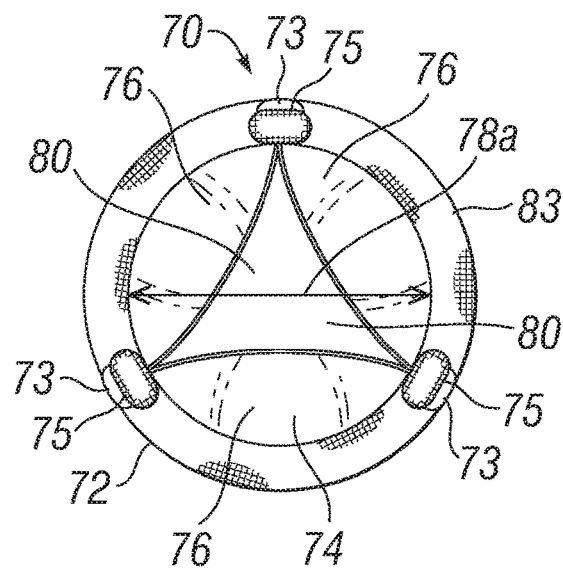
Figure 2C:
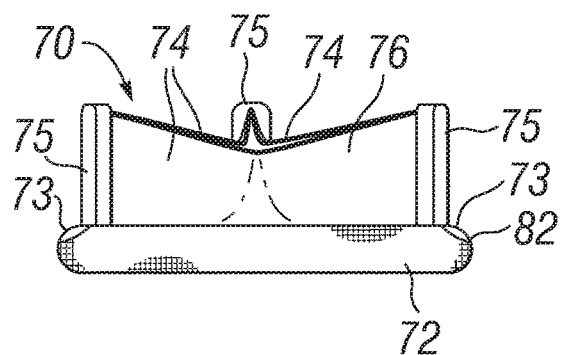

FIGS. 2A-2C depict a prosthetic heart valve 70 according to an embodiment of the invention, where the prosthetic heart valve 70 comprises a support frame 72 and valve structure 74. In the particular embodiment depicted, the valve structure 74 comprises three heart valve leaflets 76. The prosthetic heart valve 70 has an inner diameter 78a of a valve orifice 80 through which blood may flow in one direction, but the valve leaflets 76 will prevent blood flow in the opposite direction. The support frame 74 is generally rigid and/or expansion-resistant in order to maintain the particular shape (which in this embodiment is generally round) and diameter 78a of the valve orifice 80 and also to maintain the respective valve leaflets 76 in proper alignment in order for the valve structure 74 to properly close and open. The particular support frame 74 also includes commissure supports 75. In the particular embodiment depicted in FIGS. 2A-2C, the support frame 74 defines a generally rigid and/or expansion-resistant ring 82 which encircles the valve 70 and defines a generally round valve orifice 80, but other shapes are also within the scope of the invention, depending on the particular application (including issues such as the particular native valve to be replaced, etc.) The particular prosthetic heart valve 70 includes visualization markers 73 (such as radiopaque markers, etc.), which in the current embodiment are on the support frame 74 and correspond to the ring 82 and also to the commissure supports 75 (and hence to the commissures), which can aid in proper placement of a subsequently-deployed expandable prosthetic heart valve within the valve orifice 80 of the prosthetic heart valve 70.

Figure 2D:
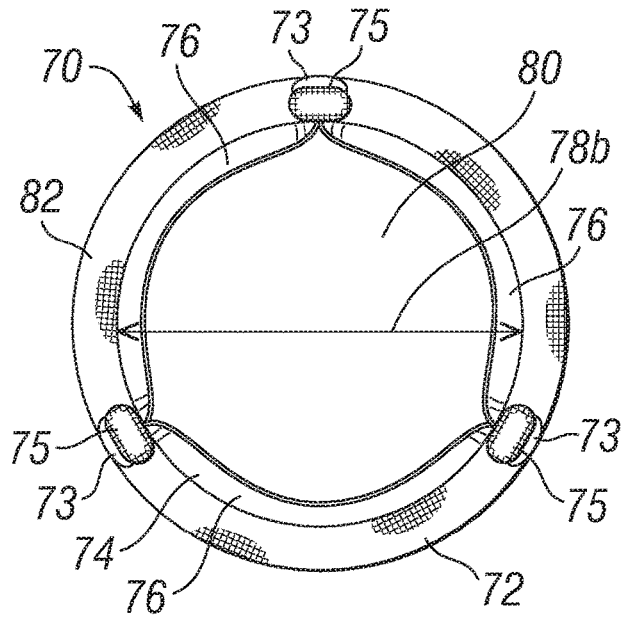
FIG. 2D depicts a top view of the prosthetic heart valve of FIGS. 2A-2C after the prosthetic heart valve has been dilated.

When the prosthetic heart valve 70 of FIGS. 2A-2C is subjected to a dilation force (such as that from a dilation balloon, which may provide pressures of 1 to 5 atmospheres), the prosthetic heart valve will be expanded somewhat. The support frame 74 will transition from the generally rigid and/or expansion-resistant configuration of FIGS. 2A-2C to a generally non-rigid and expanded configuration depicted in FIG. 2D. Note that the ring 82, which was generally rigid and/or expansion-resistant, is now generally non-rigid and is expanded, and the valve orifice 80 has accordingly been enlarged to a larger inner diameter 78*b*. The larger inner diameter 78*b* is configured to receive an expandable prosthetic heart valve therein. The overall result is that the "post-dilation" prosthetic heart valve 70 of FIG. 2D has a generally larger inner diameter circular opening 78*b*. The actual inner diameters will depend on the particular application, including aspects of the particular patient's heart (e.g., native valve and/or annulus diameter, etc.). As an example, the pre-dilation inner diameter 78*a* for a mitral valve may be between 25-33 mm, or for an aortic valve 18-28 mm. The post-dilation inner diameter 78*b* will be larger, and more specifically large enough to accommodate the outer diameter of an expandable prosthetic valve therein.

In some procedures where an expandable prosthetic heart valve is used to replace/repair a previously-deployed prosthetic heart valve, it may be desirable for the expandable prosthetic heart valve to have a deployed (expanded) inner diameter (and corresponding expandable prosthetic heart valve orifice area) approximately equal to the pre-dilation inner diameter 78*a* (and corresponding pre-dilation prosthetic valve orifice area) of the previously-deployed prosthetic heart valve 70. Such consistency between inner diameters/orifice areas can be useful in maintaining proper blood flow, so that the expandable prosthetic heart valve will provide the same blood flow as was provided by the previously-deployed prosthetic heart valve. Note that the term "valve orifice area" refers to the area of the valve orifice when the valve portion is in the fully open configuration (e.g., with the valve leaflets in their fully open configuration so that the effective orifice area is at its maximum size).

For example, Edwards Lifesciences has Sapien™ expandable prosthetic heart valves having outer diameters of 23 and 26 mm, respectively, which have corresponding inner diameters of about 20 and 23 mm, respectively. Accordingly, the post-dilation inner diameter 78*b* of the (previously-deployed) prosthetic heart valve may be on the order of 23 and 26 mm (respectively) to accommodate such expandable prosthetic heart valves. This corresponds to a post-dilation inner diameter 78*b* being about 10 to 20% larger than the pre-dilation inner diameter 78*a*. Accordingly, embodiments of the invention include a prosthetic heart valve having a post-dilation inner diameter 78*b* that is about 10, 15, or 20%, or between 5-25%, 10-20%, or 13-17% of the pre-dilation inner diameter 78*a*.

Note that the invention is not limited to the above differences between pre- and post-dilation inner diameters. For example, there may be applications where much smaller and/or much larger post-dilation inner diameters may be required. In some cases an expandable prosthetic heart valve will have an outer diameter only slightly larger than its inner diameter, so that less expansion of the previously-deployed prosthetic heart valve inner diameter is required in order to accommodate the expandable prosthetic heart valve. In other cases an expandable prosthetic heart valve may have an outer diameter that is much larger than its inner diameter, so that a greater expansion of the previously-deployed prosthetic heart valve inner diameter is necessary to accommodate the expandable prosthetic heart valve. There may also be applications where it may be desirable to deploy an expandable prosthetic heart valve having a smaller or larger inner diameter than was provided by the (previously-deployed and pre-dilation) prosthetic heart valve.

Note that, depending on the particular embodiment, a prosthetic heart valve 70 according to the invention may return to its pre-dilation inner diameter 78*a* after being subject to dilation such as from a balloon dilation catheter. However, the balloon dilation will have rendered the "post-dilation" prosthetic heart valve 70 into a generally non-rigid and/or expansion-friendly configuration, so that the "post-dilation" prosthetic heart valve 70 will be forced with relative ease into a larger diameter (such as 78*b*) when an expandable (e.g., balloon-expandable, self-expanding, etc.) prosthetic heart valve is deployed within the valve orifice 80 of the prosthetic heart valve 70.

Figure 3A:
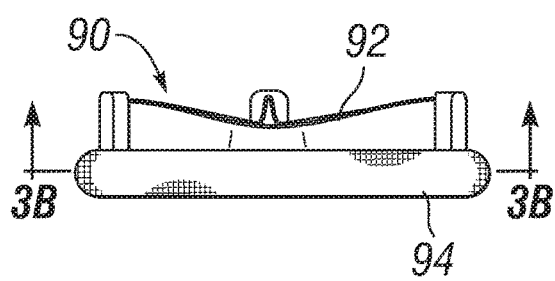
FIGS. 3A-3C depict side, top (in cross section), and close-up sectional views, respectively, of a prosthetic heart valve support structure according to an embodiment of the invention.
Figure 3B:
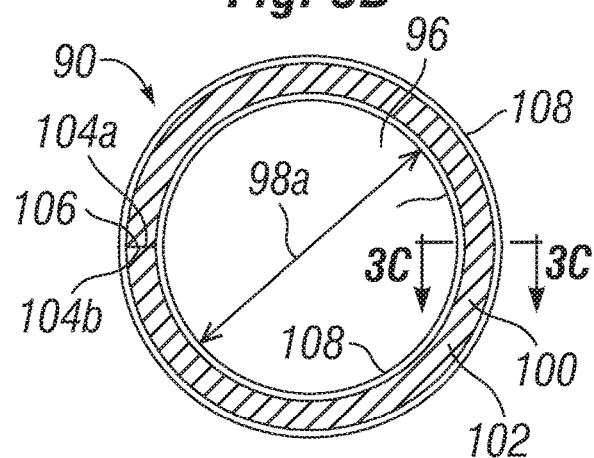
Figure 3C:
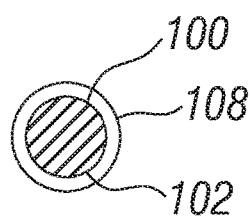

FIGS. 3A-3C depicts a prosthetic heart valve 90 having a valve structure 92 and support frame 94 according to a further embodiment of the invention, with the prosthetic heart valve 90 having a valve orifice 96 having an inner diameter 98*a*. The support frame 94 has a generally rigid and expansion-resistant core 100 formed from a single core element 102 which is bent or otherwise formed into a generally circular shape with opposing ends 104*a*, 104*b* meeting at a seam 106 so as to form the complete circle. The seam 106 may include adhesive, solder, welds, etc. in order to secure the two ends 104*a*, 104*b* together. The prosthetic heart valve 90 includes a covering 108 around the support core 96. The covering 108 may be a cloth-like material, and may be a sewing ring configured to be sewn to the native heart valve annulus during deployment of the prosthetic heart valve 90. The covering 108 is generally flexible, and may be generally elastic. The covering 108 (or a portion thereof) may also be generally compressible, especially in the portion facing inward toward the valve orifice 96, which can assist in seating an expandable valve therein. A compressible material may be applied onto or within the covering 108 in a position to provide a compressible region on the surface facing inward toward the valve orifice 96.

Figure 3D:
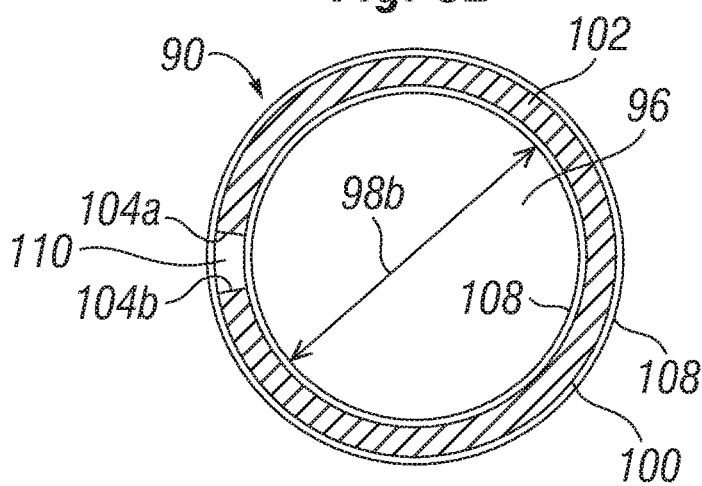
FIG. 3D depicts a top view of the prosthetic heart valve support structure of FIGS. 3A-3C after the prosthetic heart valve support structure has been dilated.

When the prosthetic heart valve 90 is subject to a dilation force such as that from a dilation balloon catheter, the support frame 94 will become non-rigid and expanded. More particularly, the seam 106 of the core 100 will rupture, so that the opposing ends 104*a*, 104*b* will be separated by an opening 110, and the core 100 will assume a generally C-shaped configuration as depicted in FIG. 3D. The covering 108 will stretch or otherwise expand circumferentially to accommodate the enlarged/expanded core 100, and the prosthetic heart valve 90 will have an enlarged inner diameter 98*b* for the valve orifice 96. Depending on the particular embodiment, including the particular construction of the core 100 and/or covering, the (post-dilation) prosthetic heart valve 90 may provide an inward (i.e., compressive) force toward the valve orifice 96. For example, the core 100 may be formed of a generally resilient spring-like material and/or memory material, and may be biased somewhat toward its non-dilated configuration (i.e., with the opposing ends 104*a*, 104*b* touching each other as in FIGS. 3A-3C). The covering 108 may also (or alternatively) be elastic and, after dilation of the prosthetic heart valve 90, may provide an inward pull on the core 100 so as to bias the opposing ends 104a, 104b toward each other. This inward pressure can help to seat an expandable heart valve that may be deployed within the prosthetic heart valve 90. In an embodiment where compressible material is provided (e.g., as part of the covering 108) facing inward toward the valve orifice 96, then the compressible material can provide additional assistance in seating an expandable heart valve within the prosthetic heart valve 90.

Figure 4A:
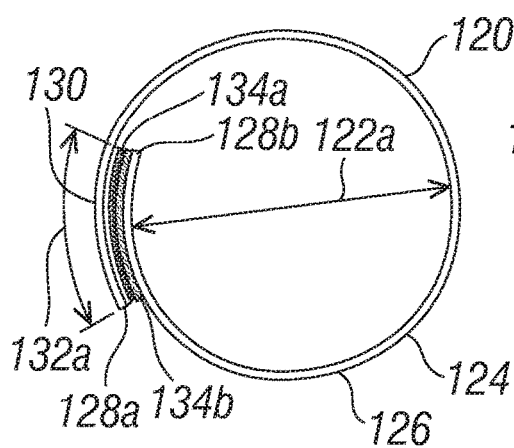
FIGS. 4A-4B depict top views of a prosthetic heart valve support structure in pre-dilation and post-dilation configurations, respectively, according to an embodiment of the invention.

FIG. 4A depicts a further embodiment of a support frame 120 for use with a prosthetic heart valve according to the invention. The support frame 120 is generally circular and defines an inner diameter 122a, and has a generally rigid core 124 formed from a single core element 126 which is bent or otherwise formed into a generally circular shape with opposing ends 128a, 128b which meet and connect at an overlapping section 130 having a length 132a. The overlapping section 130 may include adhesive, solder, welds, mechanical connections, etc. in order to secure the overlapping ends 128a, 128b together. In the particular embodiment depicted, the overlapping section 130 has a ratchet-like assembly formed from interacting portions 134a, 134b at or adjacent the opposing ends 128a, 128b. The support frame 120 may include a covering (not shown) around the core 124.

Figure 4B:
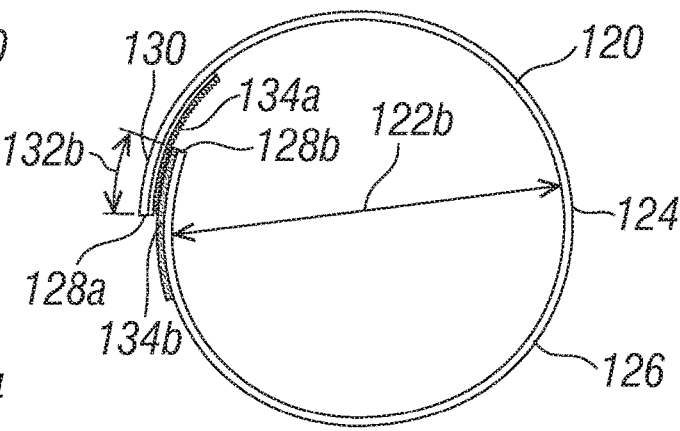

FIG. 4B depicts the support frame 120 of FIG. 4A after it has been subjected to a dilation force. The support frame 120 has been expanded to a larger inner diameter 122b, with the core 124 enlarged so that the overlapping section 130 is smaller, having a new shorter length 132b. The dilation force caused the interacting portions 134a, 134b to temporarily release their connection to permit the relative movement of the overlapping ends 128a, 128b, but with the dilation force removed the interacting portions 134a, 134b once again form a connection, so that the support frame 120 is again generally rigid. Note that, depending on the particular application, a support frame could be formed similar to that of FIGS. 4A-4B but with the interacting portions configured so that no fixed connection is formed between the overlapping ends after dilation, so that the support frame will be generally non-rigid after the dilation force has been applied. In such an embodiment, the support frame may be configured to provide (after dilation) an inward (compressive) force upon any expandable prosthetic valve that may be deployed within the valve orifice of the original (and now dilated) prosthetic valve. This inward compressive force may help to seat and otherwise hold the expandable prosthetic valve in its desired position within the native valve annulus and also within the now-dilated (prior) prosthetic valve.

Figure 5A:
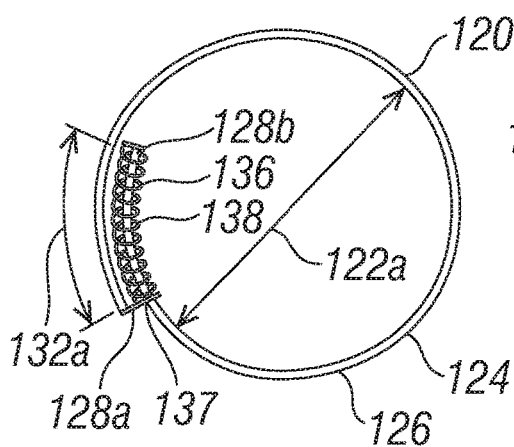
FIGS. 5A-5B depict top views of a prosthetic heart valve support structure in pre-dilation and post-dilation configurations, respectively, according to an embodiment of the invention.
Figure 5B:
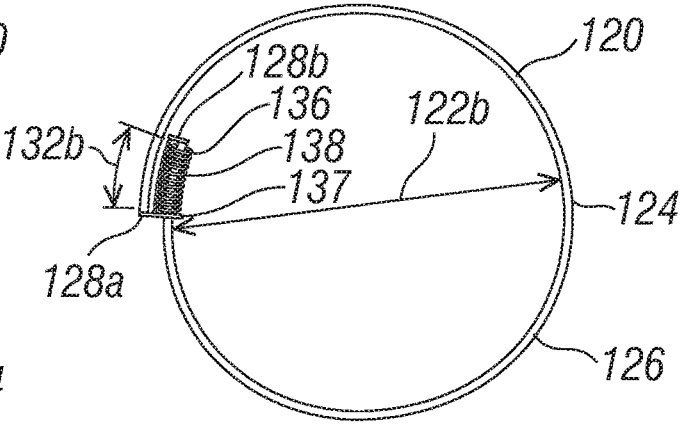

FIGS. 5A-5B depict a further embodiment of a support frame 120 for use with a prosthetic heart valve according to the invention. The support frame 120 is similar to that depicted in FIG. 4A, except the overlapping section 130 includes a sliding mechanical connection 136 having a slot 137 secured to one opposing end 128a, the second opposing end 128b having been passed through the slot 137 to form the overlapping section 130, and also including a spring 138 extending from the slot 137 to the second opposing end 128b. The spring 138 permits expansion and/or contraction of the support frame 120, with the spring 138 generally biasing the support frame 120 toward a smaller diameter, such as the smaller inner diameter 122a of FIG. 5A, but also permitting the support frame 120 to be expanded, when subject to an outside force such as a dilation balloon and/or expandable prosthetic valve, to a larger diameter such as the inner diameter 122b of FIG. 5B. Note that the spring 138 can also permit the support frame 120 (and associated valve annulus) to move with physiological annular dynamic motion, e.g., to make smaller expansions and/or contractions in response to normal valve function/heart movement as the patient's heart beats and pumps blood through the valve. The support frame 120 may include a covering (not shown) around the core 124. The support frame 120 may be formed of various materials, including elgiloy. The spring 138 can be configured to provide a specific force in opposing expansion of the support frame 120, and may be configured so that the force provided is insufficient to oppose the dilation force from a dilation balloon and/or expandable stent which might be expanded within the support frame 120. The spring 138 could be formed from traditional coil springs, compressible materials, pleated sewing rings, accordion sewing rings, and other configurations configured to provide a spring-like force.

Figure 6E:
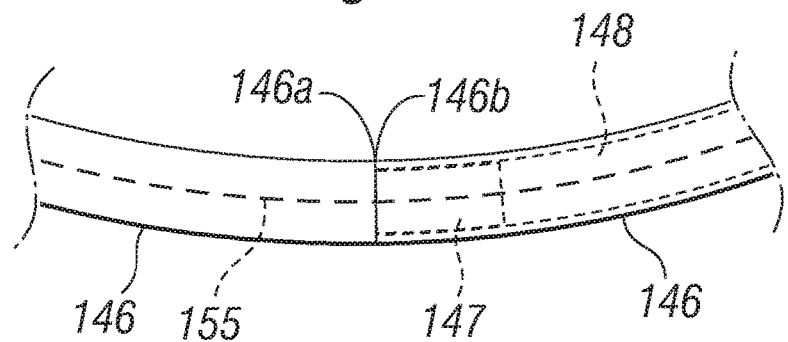
FIGS. 6E and 6F depict close-up top views of a portion, in expanded and unexpanded configurations, respectively, of a prosthetic heart valve support structure according to an embodiment of the invention.

In another embodiment of the invention, a prosthetic heart valve includes a support frame having a rigid and/or expansion-resistant core configured to separate into a plurality of pieces when subjected to a dilation force. Such a rigid and/or expansion-resistant core could be formed as a single piece, which might include one or more weak points that are subject to separation when subjected to a dilation force. In one embodiment a rigid and/or expansion-resistant core could be formed from a plurality of segments positioned in edge-to-edge fashion and configured to separate when subjected to a dilation force. FIGS. 6A-6C depict one such embodiment of a support frame 140 for use with a prosthetic heart valve according to the invention. The support frame 140 is generally circular (although other shapes are within the scope of the invention) and defines an orifice 141 having an inner diameter 142a, and has a generally rigid and/or expansion-resistant core 144 formed from multiple core segments 146 which are arranged in edge-to-edge fashion to form the generally circular shape of the core 144. Each segment 146 has an inner lumen 148, with the segments 146 when assembled into the core 144 forming a continuous core lumen 150.

Adjacent segments 146 join at seams 152, which may include adhesive, solder, welds, etc. in order to secure and/or seal the seam 152 between the adjacent segments 146. The support frame 140 has a pre-dilation cord 154 and a post-dilation cord 156 passing through the core lumen 150. The pre-dilation cord 154 may be a generally inelastic cord which is sufficiently tight to hold adjacent segments together and to prevent unwanted dilation of the support frame 140. A covering (not shown) may also be included to cover the core 144. The covering may be formed of cloth, and may be elastic.

Both the seams 152 and pre-dilation cord 154 are configured to fail or stretch when subjected to a dilation force, such as that provided by a dilation balloon, whereupon the support frame 140 will assume the expanded configuration depicted in FIG. 6D, with an enlarged inner diameter 142b. For example, the pre-dilation cord 154 may be an inelastic cord configured to fail when subject to a selected force, such as 1, 2, 3, 4, or more atmospheres, which are within the range of forces provided by many dilation balloons used in percutaneously-deployed heart valve procedures. In one embodiment, the seams 152 are merely sealed, with the sealant providing little if any securement against separation of adjacent segments 146. In such an embodiment, the pre-dilation cord 154 may serve as the sole device to hold the core segments 146 together in the rigid and/or expansion-resistant (pre-dilation) configuration. Once the pre-dilation cord 154 fails or stretches due to the dilation pressure, essentially all of the seams 152 will separate so that adjacent segments 146 separate with spaces 158 separating the adjacent segments 146. The remaining portions of the pre-dilation cord 154 remain within the support frame 140 after dilation.

The post-dilation cord 156 remains intact after dilation and may serve to hold the support frame 140 together post-dilation. The post-dilation cord 156 could be elastic, and/or could be inelastic and have a larger diameter, and possibly a higher failure strength, than the pre-dilation cord 154. If the post-dilation cord 156 is elastic, it may provide an inward compressive force into the central orifice 141. If the post-dilation cord 156 is generally inelastic, it will remain intact after dilation either because its strength was too great to be ruptured by the dilation balloon or because it had a diameter that was larger than that of the inflated dilation balloon.

In a variation of the embodiment of FIGS. 6A-6D, the pre-dilation cord 154 could be left out of the support frame 140, and the seams 152 themselves could have adhesive or other connections that serve to hold the segments 146 together prior to dilation. In a further variation, the pre-dilation cord 154 could be left out of the support frame, with a post-dilation cord 156 configured to be elastic and with sufficient strength/elasticity to provide an inward compressive force into the central orifice with sufficient strength to hold the segments 146 together prior to dilation, but with the inward compressive force weak enough to permit the support frame 140 to be dilated and to permit an expandable prosthetic heart valve to be deployed therein. Accordingly, the post-dilation cord 156 would serve as both pre-dilation cord and post-dilation cord.

Visualization references (such as the visualization markers 73 from FIGS. 2A-2D) may be included on or in various portions of the device. For example, visualization references may be placed on, in, or adjacent the support frame 140, core 144, segments 146, pre-dilation cord 154, and/or post-dilation cord 156, etc. in the device of FIGS. 6A-6D. Such visualization references can help a user to properly position a dilation balloon and/or subsequently-deployed expandable prosthetic heart valve within the previously-deployed prosthetic heart valve having the support frame 140. For example, visualization markers positioned at the generally rigid support frame 140 (or more specifically at the segments 146 and/or the pre-dilation cord 154 and/or post-dilation cord 156) could be used to guide delivery and expansion of a dilation balloon, and also to confirm that the support frame 140 has been dilated. The visualization markers could also be used to guide delivery and expansion of the expandable prosthetic heart valve within the support frame 140, and to confirm proper deployment of the expandable prosthetic heart valve.

Figure 6F:
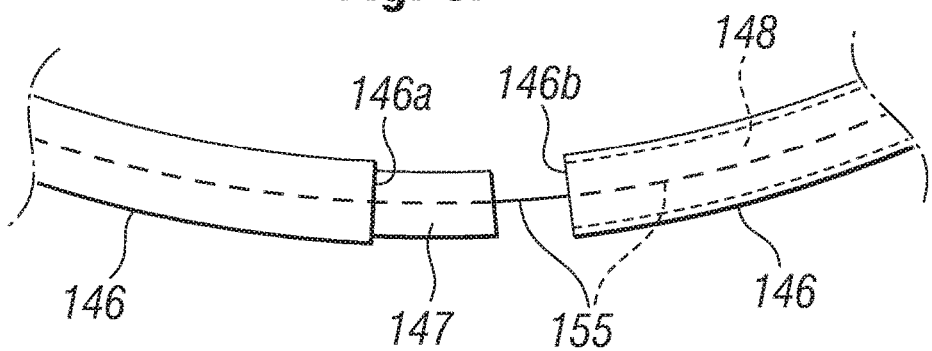

The support frame 140 may have segments 146 having ends 146a, 146b which interlock and/or otherwise interact in order to hold the segments 146 together and/or in alignment. As depicted in the close-up view of FIG. 6E, adjacent segments 146 may include interconnecting ends 146a, 146b, with one end 146a having a member 147 configured to be received within the lumen 148 or other opening in an end 146b of an adjacent segment 146. The interconnecting ends 146a, 146b keep the adjacent segments 146 in a desired alignment so that the segment ends 146a, 146b cannot slide sideways with respect to the member 147 and lumen 148, but does permit the segments 146 to be pulled apart, as depicted in FIG. 6F, in order to permit expansion of the support frame 140 (as was depicted in FIG. 6D). The pulling apart of the segments 146 may be opposed by various structures set forth herein which oppose and/or restrict dilation of a support frame, such as one or more elastic and/or inelastic cords 155 configured to oppose and/or restrict dilation of the support frame as was depicted in FIGS. 6A-6D.

Figure 7A:
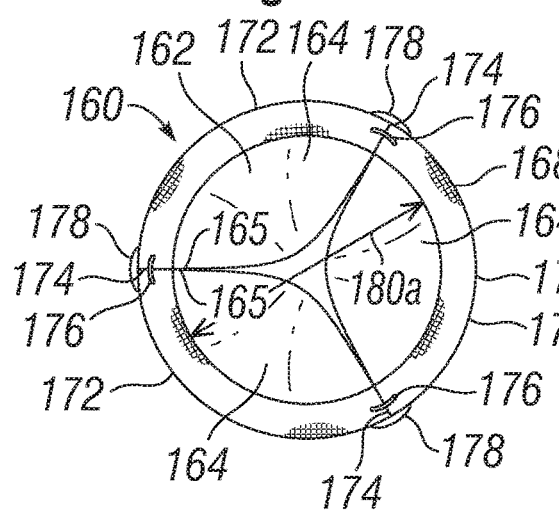
FIGS. 7A and 7B depict top views of unexpanded and expanded configurations, respectively, of a prosthetic heart valve support structure according to an embodiment of the invention.
Figure 7B:
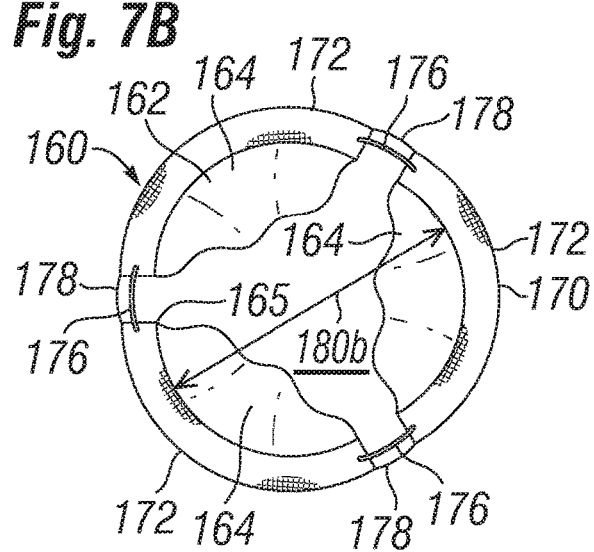

FIGS. 7A-7B depict a further embodiment of the invention, with a prosthetic heart valve 160 having a valve structure 162 formed from three (3) leaflets 164 spaced around the valve orifice 166. The support frame 168 includes a core 170 formed from three (3) segments 172. At the base/perimeter of the valve structure 162, the edges 165 of each leaflet 164 coincide with the edges of each respective segment 172 as well as the seams 174 (and the commissure supports, if present). Adjacent segments 172 are connected to each other at the seams 174, such as with adhesive(s), weld(s), etc., in order to form the rigid and/or expansion-resistant (pre-dilation) support frame 168. Adjacent segments 172 are also connected via individual inelastic cords 176 and elastic cords 178 extending between the adjacent segments 172. As depicted in FIG. 7A, the (pre-dilation) prosthetic valve 160 has a valve orifice 166 having an inner diameter 180a. A cloth cover (not shown) or similar covering will also typically be included to cover the support frame 168 and its associated elements (e.g., inelastic cords 176 and elastic cords 178).

When the prosthetic heart valve 160 of FIG. 7A is subjected to a dilation force, the seams 174 between the segments 172 will fail and the support frame 168 will separate into the three segments 172, as depicted in FIG. 7B. Note that in this particular embodiment the inelastic cords 176 do not serve to hold adjacent segments against each other, but instead permit adjacent segments to separate when subjected to a dilation force. The inelastic cords 176 prevent excessive separation between any adjacent segments 172 as the dilation balloon (or other dilation force) is applied, with the result being that the segments 172 will all be spaced generally equally apart from each other once the full dilation force is applied. After the dilation force is removed, the elastic cords 178 will serve to pull the adjacent segments toward each other and to provide a generally inward (compressive) pressure to the valve orifice 166 but while also maintaining the post-dilation inner diameter 180b (FIG. 7B) at a larger size than the pre-dilation diameter 180a (FIG. 7A). Because the leaflets 164 were positioned with their base edges coinciding with the seams 174 between segments 172, the leaflets 164 can remain generally intact after dilation and still permit the segments 172 to separate to form the enlarged inner diameter 180b. Note, however, that deploying a new expandable prosthetic valve within the prosthetic heart valve 160 will generally involve deploying an expandable heart valve support stent that will crush the leaflets 164 of the current prosthetic heart valve 160 against the support frame 168, walls of the native valve annulus, and/or lumen.

If the prosthetic heart valve 160 includes commissure supports (not shown) on the support frame 168, the commissure supports can be positioned on or adjacent the seams 174 between segments 172, and the commissure supports can also be configured to split lengthwise when the prosthetic heart valve 160 is dilated so that one-half of each commissure support will remain with the adjacent segment 172 on either side of said commissure support. In such an embodiment, the edges of the valve leaflets 164 can be secured (e.g., during assembly of the prosthetic heart valve 160) to the respective half of each commissure support, so that when the prosthetic heart valve 160 is dilated adjacent leaflets 164 can separate from adjacent leaflets 164, but each leaflet 164 will still remain secured via its edges to its respective commissure support halves.

There are many variations of the above-cited embodiments, including various combinations of the various embodiments. For example, the pre-dilation cord 154 and/or post-dilation cord 156 of FIGS. 6A-6D could be used with the core 100 of FIGS. 3A-3D in order to provide inward compressive force after the core 100 was dilated. The post-dilation cord 156 of FIGS. 6A-6D could be replaced by a cover 108 such as that depicted in FIGS. 3A-3D, with the cover 108 serving to hold the post-dilation core assembly (including any segments and/or pieces thereof) together and also (if formed form elastic material) providing an inward compressive force to the valve orifice.

FIG. 8A depicts an expandable prosthetic heart valve deployment catheter 220 configured for (prior) prosthetic heart valve dilation and (replacement) expandable prosthetic heart valve deployment. The deployment catheter 220 has an elongated main body 222, a proximal end 224, and a distal end 226. The proximal end 224 includes a handle 228. The distal end 226 includes a dilation balloon 230 upon which an expandable prosthetic valve 232 is mounted. In the particular embodiment depicted, the expandable prosthetic valve 232 includes a stent 234. The distal end 226 may also include one or more radiopaque markers 233 or similar visibility markers to improve visibility of the device within the patient when using fluoroscopy or other viewing technologies.

FIGS. 8B-8D depict deployment of an expandable prosthetic heart valve 232 within a heart valve annulus 236 where a prosthetic heart valve 10 has previously been deployed. The previously-deployed prosthetic heart valve 10 may have been deployed using any methods, including methods currently known in the art such as traditional (open chest) surgery, minimally-invasive (e.g., keyhole) surgery, and percutaneous surgery. Depending on the particular application, the previously-deployed prosthetic heart valve 10 can be deployed in the patient years prior to, days prior to, hours prior to, or immediately prior to deployment of the expandable prosthetic heart valve 232 as depicted in FIGS. 8B-8D.

FIG. 8B depicts the expandable prosthetic heart valve deployment catheter 220 of FIG. 8A with the distal end 226 advanced so that the dilation balloon 230 and expandable prosthetic heart valve 232 are positioned within the previously-deployed prosthetic heart valve 10 in the patient's heart 240. The previously-deployed prosthetic heart valve 10 is seen in cross-section to show the generally rigid and/or expansion-resistant support frame 238.

In the particular embodiment depicted in FIG. 8B, the deployment catheter 220 has been advanced over a guide wire 242, which was advanced into the patient's heart 240 and previously-deployed prosthetic heart valve 10 prior to advancement of the deployment catheter 220 into the patient. Note that the use of a guide wire 242 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 8C, once the dilation balloon 230 and expandable prosthetic heart valve 232 are properly positioned within the heart valve annulus 234 and previously-deployed prosthetic heart valve 10, the dilation balloon 230 is expanded. The expanding dilation balloon 230 forces the stent 234 to expand outwardly, and crushes the leaflets 244 of the previously-deployed prosthetic heart valve 10 against the heart valve annulus 236. The force from the expanding dilation balloon 230 also dilates the previously-deployed prosthetic heart valve 10 and heart valve annulus 236, forcing the support frame 238 of the previously-deployed prosthetic heart valve 10 to expand and/or become non-rigid.

In FIG. 8D, the dilation balloon 230 is deflated or otherwise reduced in diameter, with the new expandable prosthetic valve 232 deployed in the heart valve annulus 236 and previously-deployed prosthetic heart valve 10, and also held in place by the stent 234. The outward pressure from the expanded stent 232, along with the inward pressure from the heart valve annulus 236 and from any elastic portions (such as core, cords, and/or or covers) of the previously-deployed prosthetic heart valve 10 or from the now-crushed previously-deployed prosthetic heart valve leaflets 244, combine to firmly seat the new expandable prosthetic valve 232 in the desired position in the heart valve annulus 236 and previously-deployed prosthetic heart valve 10. The deployment catheter 220 with the dilation balloon 230 can then be withdrawn from the heart 240, leaving the new expandable prosthetic heart valve 232 in its deployed position within the patient and the previously-deployed prosthetic heart valve 10.

In a further embodiment of the invention, the previously-deployed prosthetic heart valve 10 is dilated in a separate step from deployment of the expandable prosthetic heart valve 232. FIG. 9A depicts an expandable prosthetic heart valve deployment catheter 220 configured for previously-deployed prosthetic heart valve dilation and expandable prosthetic heart valve deployment using two separate balloons, and more specifically a distal balloon 230a and a proximal balloon 230b. The distal balloon 230a is configured to deploy the new expandable prosthetic valve 232, which is positioned on the distal balloon 230a, whereas the proximal balloon 230b is configured for dilation of the previously-deployed prosthetic heart valve 10.

FIGS. 9B-9D depict dilation of the previously-deployed prosthetic heart valve 10 and valve annulus 236 using the proximal balloon 230b. In FIG. 9B, the deployment catheter 220 has been advanced into the heart 230 with the distal balloon 230a (with expandable prosthetic valve 232 thereon) advanced past the previously-deployed prosthetic heart valve 10, and the proximal balloon 230b positioned within the previously-deployed prosthetic heart valve 10 and valve annulus 236.

The proximal balloon 230b is inflated or otherwise expanded, as depicted in FIG. 9C, thereby dilating the previously-deployed prosthetic heart valve 10 and valve annulus 236. The support frame 238 of the previously-deployed prosthetic heart valve 10 is expanded and/or assumes a generally non-rigid configuration, similarly to the changes previously discussed with respect to the dilation discussed in FIG. 8C above.

After dilation of the previously-deployed prosthetic heart valve 10, the proximal balloon 230b is deflated or otherwise reduced in diameter, as depicted in FIG. 9D. The deployment catheter 220 may then be withdrawn from the patient until the proximal balloon 230b is proximal of the previously-deployed prosthetic heart valve 10 and the distal balloon 230a is positioned within the previously-deployed prosthetic heart valve 10. The distal balloon 230a will be positioned within the previously-deployed prosthetic heart valve 10 in a similar fashion to that depicted for balloon 230 in FIG. 8B. The distal balloon 230a will then be expanded to deploy the expandable prosthetic valve 232 in essentially the same manner as was discussed and depicted in FIGS. 8B-8D. The distal balloon 230a will serve to deploy the new expandable prosthetic valve 232, and may also serve to further dilate the previously-deployed prosthetic heart valve 10 and/or native valve annulus 236.

Note that the expandable prosthetic valve may be self-expanding, in which case the deployment catheter may not have a dilation balloon as depicted in FIGS. 8A-8D and 9A-9D. Moreover, such a self-expanding prosthetic heart valve could be deployed with or without prior dilation of the previously-deployed prosthetic heart valve. For example, a self-expanding prosthetic heart valve may provide sufficient outward radial force to dilate the previously-deployed prosthetic heart valve and/or to hold a now-dilated previously-deployed prosthetic heart valve in an expanded configuration in order to provide sufficient room for the self-expanding prosthetic heart valve in its expanded configuration.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A prosthetic heart valve having an inflow end and an outflow end, the prosthetic heart valve adapted for post-implant expansion and having an unexpanded configuration and an expanded configuration, the prosthetic heart valve adapted for implant at a heart valve annulus and comprising:
   a support frame surrounding a flow orifice and a one-way valve structure comprising a plurality of flexible leaflets connected to the support frame and extending across the flow orifice, the valve structure configured to permit flow through the heart valve in one direction through the flow orifice while preventing flow in the opposite direction,
   the support frame comprising a support ring extending continuously around the flow orifice having free ends that overlap and are engaged, the support ring having a first inner diameter when the heart valve is in the unexpanded configuration corresponding to a functional state of the heart valve where the valve structure functions to permit one-way flow through the orifice, the engagement of the overlapping free ends being configured to resist relative sliding movement in a first direction when the implanted heart valve is subjected to radially compressive forces imparted by normal cardiac cycling to prevent inward constriction of the support frame, and
   the support ring having a second inner diameter larger than the first inner diameter when the prosthetic heart valve is in the expanded configuration, the engagement of the overlapping free ends being configured to permit relative sliding movement in a second direction when the implanted heart valve is subjected to a dilation force significantly greater than forces associated with normal cardiac cycling, the overlapping free ends being configured to remain substantially aligned while permitting expansion of the support ring from the first to the second inner diameter, wherein the second inner diameter is such that when the heart valve is in the expanded configuration the valve structure can no longer function to permit one-way flow through the orifice.

2. The heart valve of claim 1, wherein the overlapping free ends of the support ring are welded together in the unexpanded configuration of the heart valve.

3. The heart valve of claim 1, wherein the overlapping free ends of the support ring are adhered together in the unexpanded configuration of the heart valve.

4. The heart valve of claim 1, wherein one of the overlapping free ends of the support ring extends within another one.

5. The heart valve of claim 1, wherein the overlapping free ends have a ratchet-like assembly formed therebetween which prevents contraction of the support ring while permitting expansion.

6. The heart valve of claim 1, wherein the overlapping free ends engage with a spring therebetween which prevents contraction of the support ring while permitting expansion.

7. The heart valve of claim 1, wherein the overlapping free ends engage with an inelastic member which initially prevents expansion of the support ring and fails when the implanted heart valve is subjected to a dilation force significantly greater than forces associated with normal cardiac cycling.

8. A prosthetic heart valve having an inflow end and an outflow end, the prosthetic heart valve adapted for post-implant expansion and having an unexpanded configuration and an expanded configuration, the prosthetic heart valve adapted for implant at a heart valve annulus and comprising:
   a plurality of flexible leaflets, each having a peripheral edge and a free edge, the free edges of the leaflets arranged to meet within a flow orifice defined by the valve and ensure one-way blood flow therethrough;
   an inner support frame providing peripheral support for the leaflets, the inner support frame having a generally circular periphery around an inflow end and flow orifice defining an implant circumference with a first diameter adapted to support the leaflets in normal use, at least an outflow edge of the support frame defining cusps curving toward the inflow end of the valve alternating with commissure posts extending toward the outflow end of the valve, wherein the peripheral edge of each flexible leaflet is secured along the support frame outflow edge so as to conform generally to one of the support frame cusps and up adjacent commissure posts, the support frame including at least one expandable section located at one of the commissure posts formed by overlapping free ends thereof that are engaged and permit expansion of the support frame from the first diameter to a second diameter larger than the first diameter upon application of an outward dilatory force from within the support frame larger than forces associated with normal use, wherein the second diameter is such that when the heart valve is in the expanded configuration the valve structure can no longer function to permit one-way flow through the orifice, the engagement of the overlapping free ends being configured to resist relative sliding movement in a first direction when the implanted heart valve is subjected to radially compressive forces imparted by normal cardiac cycling to prevent inward constriction of the support frame; and a cloth covering surrounding the support frame and facilitating attachment of the leaflet peripheral edges along the support frame outflow edge.

9. The heart valve of claim 8, wherein edges of adjacent valve leaflets are secured to one half of each of the one commissure post, so that when the prosthetic heart valve expands the adjacent leaflets separate from each other, but each leaflet remains secured via its edges to the respective one commissure post half.

10. The heart valve of claim 9, wherein there are three expandable sections each located at one of the commissure posts.

11. The heart valve of claim 8, wherein the overlapping free ends engage with an inelastic member which initially prevents expansion of the support frame and fails when the implanted heart valve is subjected to a dilation force significantly greater than forces associated with normal cardiac cycling.

12. The heart valve of claim 8, wherein the overlapping free ends engage with an elastic member which limits expansion of the support frame.

13. The heart valve of claim 8, wherein one of the overlapping free ends of the support frame extends within another one.

14. The heart valve of claim 8, wherein the overlapping free ends have a ratchet-like assembly formed therebetween which prevents contraction of the support frame while permitting expansion.

15. A prosthetic heart valve having an inflow end and an outflow end, the prosthetic heart valve adapted for post-implant expansion and having an unexpanded configuration and an expanded configuration, the prosthetic heart valve adapted for implant at a heart valve annulus and comprising:
 a plurality of flexible leaflets, each having a peripheral edge and a free edge, the free edges of the leaflets arranged to meet within a flow orifice defined by the valve and ensure one-way blood flow therethrough;
 an inner support frame providing peripheral support for the leaflets and having a generally circular support ring extending continuously around the inflow end to define the flow orifice, the support ring including at least one expandable section formed by overlapping free ends that engage and permit expansion of the support frame from a first diameter to a second diameter larger than the first diameter upon application of an outward dilatory force from within the support frame significantly greater than normal cardiac cycling, the engagement of the overlapping free ends being configured to resist relative sliding movement in a first direction when the implanted heart valve is subjected to radially compressive forces imparted by normal cardiac cycling to prevent inward constriction of the support frame, the engagement of the overlapping free ends also being generally resistant to expansion until the support ring is subjected to an outward dilatory force of at least 1 atmosphere, the free ends being engaged to maintain circularity of the support ring when expanded from the first diameter to the second diameter, wherein the second diameter is such that when the heart valve is in the expanded configuration the valve structure can no longer function to permit one-way flow through the orifice; and
 a cloth covering surrounding the support frame and facilitating attachment of the leaflet peripheral edges to the support frame.

16. The heart valve of claim 15, wherein the cloth covering is elastic and sized to stretch when the heart valve transitions from its unexpanded configuration to its expanded configuration and provide an inward force to the support ring so as to bias the overlapping free ends toward each other.

17. The heart valve of claim 15, wherein the overlapping free ends engage with an inelastic member which initially prevents expansion of the support ring and fails when the implanted heart valve is subjected to an outward dilatory force of at least 1 atmosphere.

18. The heart valve of claim 15, wherein at least an outflow edge of the support frame defines cusps curving toward the inflow end of the valve alternating with commissure posts extending toward the outflow end of the valve, wherein the peripheral edge of each flexible leaflet is secured along the support frame outflow edge so as to conform generally to one of the support frame cusps and up adjacent commissure posts, and wherein there are multiple expandable sections around the support ring.

19. The heart valve of claim 18, wherein the multiple expandable sections are located coincident with the commissure posts.

20. The heart valve of claim 19, wherein the edges of adjacent valve leaflets are secured to one half of adjacent commissure posts which are separable, so that when the prosthetic heart valve expands the adjacent leaflets separate from each other.

* * * * *